United States Patent [19]

Yamaguchi et al.

[11] 4,287,366
[45] Sep. 1, 1981

[54] PROCESS FOR PREPARING BISPHENOL SULFONE DERIVATIVES

[75] Inventors: Akihiro Yamaguchi, Yokohama; Keizaburo Yamaguchi, Kawasaki; Hisamichi Murakami; Tadashi Kobayashi, both of Yokohama, all of Japan

[73] Assignee: Mitsui Toatsu Chemicals, Inc., Tokyo, Japan

[21] Appl. No.: 128,712

[22] Filed: Mar. 10, 1980

[51] Int. Cl.$^3$ .............................................. C07C 147/10
[52] U.S. Cl. ...................................... 568/33; 560/11; 562/429
[58] Field of Search .................... 568/33; 562/429; 560/11

[56] References Cited

U.S. PATENT DOCUMENTS

| | | | |
|---|---|---|---|
| 2,661,376 | 12/1953 | Comer et al. | 568/37 |
| 3,449,439 | 6/1969 | Kuhnen et al. | 568/33 |
| 4,089,904 | 5/1978 | Cisney et al. | 568/33 |
| 4,108,866 | 8/1978 | Tramier et al. | 568/37 |

FOREIGN PATENT DOCUMENTS 48-43725 12/1973 Japan.

OTHER PUBLICATIONS

S. Suyama et al., Chem. Abstracts 81:13110h (1974), Organic Sulfones.
Gump et al., J. Am. Chem. Soc., 67, pp. 238–240 (1945).
Nikolenko et al., J. Gen'l. Chem. USSR, 33, pp. 3364–3365 (1963).
Drabowicz et al., A Facile and Selective Oxidation of Organic Sulphides to Sulphoxides with Hydrogen Peroxide/Selenium Dioxide System, *Synthesis*, pp. 758–759, (Oct. 1978).
Laba, V. et al., Chem. Abstracts, 86:120989s (1977) Sulfoxides.

*Primary Examiner*—Donald G. Daus
*Assistant Examiner*—M. C. Eakin
*Attorney, Agent, or Firm*—Fisher, Christen & Sabol

[57] ABSTRACT

A process for preparing bisphenol sulfone derivatives represented by the general formula (I)

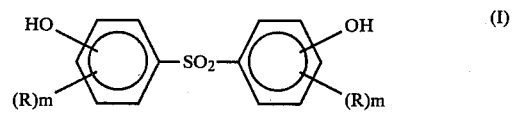

where R stands for hydrogen, a halogen, an alkyl radical, a cycloalkyl radical, an aryl radical, an aralkyl radical, hydroxyl group, an alkoxy radical, allyloxy group, carboxyl group, or a carboalkoxy radical, m is an integer of from 1 to 3, and when m is 2 or more, R may be identical to or different from each other, and adjacent Rs may be combined to form a ring, by oxidizing with hydrogen peroxide a compound represented by the general formula (II)

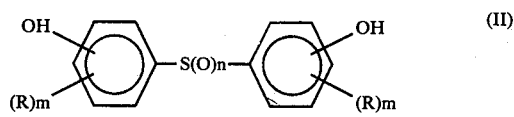

where R and m have the same meanings as defined for the formula (I), and n is zero or 1, in the presence of an alkali in an amount more than the equimolar amount thereof relative to said compound in water and/or an organic solvent which do not form any organic peracids under reaction conditions.

13 Claims, No Drawings

PROCESS FOR PREPARING BISPHENOL SULFONE DERIVATIVES

BACKGROUND OF THE INVENTION

1. Field of the Invention

This invention relates to a novel process for preparing bisphenol sulfone derivatives.

2. Description of the Prior Art

Generally, the oxidation of sulfur compounds is effected in a glacial acetic acid solution by using solely hydrogen peroxide as oxidizing agent (peracetic acid oxidation).

The following have been known about the process in which bisphenol sulfides or bisphenol sulfoxides are oxidized to obtain the corresponding sulfones.

(1) The oxidation of sulfides with hydrogen peroxide is usually effected in glacial acetic acid (peracetic acid oxidation), but it also proceeds in an organic solvent such as acetone.

(2) The oxidation of 2,2'-bisphenol sulfides with hydrogen peroxide is effected in a similar way as above in glacial acetic acid to obtain the corresponding 2,2'-bisphenol sulfone derivatives [J. Am. Chem. Soc., 67. 238 (1945)].

(3) In a conventional process, 4,4'-diphenol sulfide is oxidized in the presence of a metallic catalyst such as molybdenum, vanadium, titanium, tungsten, or the like, in an aqueous acid solution to obtain 4,4'-diphenol sulfone. 4,4'-Diphenol sulfide is subjected to heating under reflux with a pH not more than 1 in the presence of molybdenum to obtain the final product at an yield of 99.7% (purity 97.6%) (U.S. Pat. No. 4,089,904).

(4) In the case of the preparation of bisphenol sulfone by the oxidation of bisphenol sulfoxide, the 4,4'-bisphenol sulfoxide is oxidized with hydrogen peroxide in glacial acetic acid to obtain the corresponding sulfone. For example, 4,4'-diphenol sulfoxide is subjected to oxidation at 85° C. in a large excess of glacial acetic acid to obtain the final product at a yield of 85% [L. M. Nikolenko et al, J. General Chem. of USSR, 33, 3664 (1963)].

(5) Nothing is known about the oxidation reaction of 2,2'-bisphenol sulfoxides. 2,2'-Bisphenol sulfoxides are only expected to form the corresponding 2,2'-bisphenol sulfone derivatives by the peracetic acid oxidation as in 4,4'-bisphenol sulfoxide mentioned above.

However, such processes as mentioned in the above items (2), (4) and (5) have many drawbacks from the standpoints of economy as well as procedures for the preparation thereof in effecting these reactions on an industrial scale, because the oxidation reaction is effected in a large excess of peracetic acid, so that the handling thereof requires to take bumpings and explosions into consideration, and because a large amount of glacial acetic acid is used and discharged into a large amount of waste water, which requires a large amount of expenditure including that for the waste liquor disposal and so forth.

The process described in the above item (3) cannot be regarded as economical and advantageous for industrial purposes due to the following reasons. In the process, a relatively expensive metallic catalyst is used, and the recovery thereof requires complicated procedures and many problems associated with environmental protections take place, because the catalyst is dissolved in the aqueous solution. Moreover, the process has such problems that the reaction conditions especially of pH remarkably affect the yield and purity of the final product, that the product is colored, and so forth.

SUMMARY OF THE INVENTION

An object of this invention is to provide a novel and industrially advantageous process for preparing bisphenol sulfone derivatives.

Another object of this invention is to provide a novel process for preparing bisphenol sulfones of high purity at a high yield.

According to this invention there is provided a process for preparing bisphenol sulfone derivatives represented by the general formula (I)

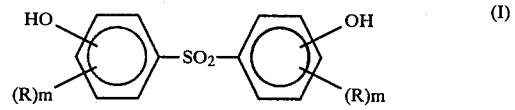

where R stands for hydrogen, a halogen, an alkyl radical, a cycloalkyl radical, an aryl radical, an aralkyl radical, hydroxyl group, an alkoxy radical, allyloxy group, carboxyl group, or a carboalkoxy radical, m is an integer of from 1 to 3, and when m is 2 or more, R may be identical to or different from each other, and adjacent Rs may be combined to form a ring, which comprises oxidizing with hydrogen peroxide a compound represented by the general formula (II)

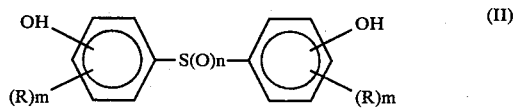

where R and m have the same meanings as defined for the formula (I), and n is zero or 1, in the presence of an alkali in an amount more than the equimolar amount thereof relative to said compound in a solvent selected from the group consisting of water and organic solvents which do not form any organic peracids under reaction conditions to form said bisphenol sulfone derivatives.

DETAILED DESCRIPTION OF THE INVENTION

In accordance with the present invention, the compounds represented by the general formula (II), that is, bisphenol sulfides (when n=0 in the formula (II)) and bisphenol sulfoxides (when n=1 in the formula (II)) form the corresponding phenolates with an alkali in an amount which is more than the equimolar amount thereof relative to the starting material of formula II. The reaction of the phenolate with a theoretical amount of hydrogen peroxide causes the oxidation to proceed desirably, and after the completion of the reaction, the reaction mixture is neutralized to obtain bisphenol sulfone derivatives.

In accordance with the present invention, the phenolates of bisphenol sulfides or bisphenol sulfoxides in the formula (II) can be dissolved by the use of a small amount of an organic solvent which does not form any organic peracids with hydrogen peroxide under reaction conditions to effect the reaction when the phenolates are insoluble in water.

Furthermore, an organic solvent instead of water can be used regardless of the solubility of the phenolate in water, which results in an extremely improved yield of the final product per volume of the reaction mixture, because a much less amount of organic solvent is sufficient compared with the amount of water used.

Alkali is required to be used in an amount more than the equimolar amount thereof relative to bisphenol sulfides or bisphenol sulfoxides. No reaction proceeds in the absence of alkali.

In the case of bisphenol sulfides, the use of an alkali in an amount less than the equimolar amount thereof results in the incorporation of sulfoxides therein. The sulfone is formed in an amount proportional to the amount of alkali used, and the use of the equimolar amount of alkali causes sulfoxides to form sulfones entirely. On the other hand, in the case of bisphenol sulfoxides, the sulfone is formed in an amount proportional to the amount of alkali added-thereto, and the use of the equimolar amount of alkali causes formation of sulfones entirely.

Examples of the alkali used in the present invention include alkali metal hydroxide such as sodium hydroxide, potassium hydroxide, lithium hydroxide, and the like. Alkali may be used directly in the form of a solid, but generally used in the form of an aqueous solution. Alkali is usually used in an amount on the order of from the equimolar amount to 5 moles and preferably the equimolar amount to 2 moles relative to the compound of the general formula (II). However, in the case of a bisphenol having carboxyl group(s) as substituent, it is necessary to add thereto alkali in an amount equivalent to the carboxyl groups(s) to form a carboxylic acid alkali metal salt followed by adding thereto alkali in an amount more than the equimolar amount to form phenolates by adjusting the amount of alkali used.

The compounds represented by the general formula (II) include, for example, 2,2'-bisphenol compounds represented by the general formula (III)

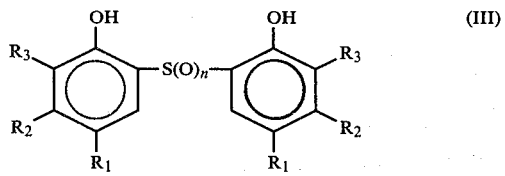

where $R_1$, $R_2$ and $R_3$ stand for hydrogen, a halogen, an alkyl radical, a cycloalkyl radical, an aryl radical, an aralkyl radical, hydroxyl group, an alkoxy radical, allyloxy group, carboxyl group or a carboalkoxy radical, being identical to or different from each other, or $R_1$ and $R_2$, $R_2$ and $R_3$ or $R_1$, $R_2$ and $R_3$ may form a ring together with the carbons of the benzene nucleus to which carbons $R_1$, $R_2$ and $R_3$ bond respectively, and n is zero or 1, such as 2,2'-bisphenol sulfides and 2,2'-bisphenol sulfoxides, and 4,4'-bisphenol compounds represented by the general formula (IV)

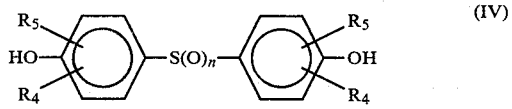

where $R_4$ and $R_5$ have the same meanings as defined for $R_1$ and $R_2$ in the general formula (II), and n is zero or 1, such as 4,4'-bisphenol sulfides and 4,4'-bisphenol sulfoxides.

More specifically, examples of the above compounds include 2,2'-bisphenol sulfides such as 2,2'-diphenol sulfide, 2,2'-bis(4-methylphenol) sulfide, 2,2'-bis(6-methylphenol)sulfide, 2,2'-bis(4-iso-propylphenol) sulfide, 2,2'-bis(4-n-butylphenol) sulfide, 2,2'-bis(4-sec-butylphenol) sulfide, 2,2'-bis(4-tertbutylphenol) sulfide, 2,2'-bis(6-tert-butylphenol) sulfide, 2,2'-bis(4-tert-amylphenol) sulfide, 2,2'-bis(4-tert-octylphenol) sulfide, 2,2'-bis(4-nonyl-phenol) sulfide, 2,2'-bis(4-tert-butyl-6-methylphenol) sulfide, 2,2'-bis(4-methyl-6-tert-butylphenol) sulfide, 2,2'-bis(4,6-dimethylphenol) sulfide, 2,2'-bis(4,6-ditert-butylphenol) sulfide, 2,2'-bis(4,5-dimethylphenol) sulfide, 2,2'-bis(4-cyclohexylphenol) sulfide, 2,2'-bis(4-cyclohexyl-6-methylphenol) sulfide, 2,2'-bis(4,6-dicyclohexyl-phenol) sulfide, 2,2'-bis(4-α,α'-dimethyl-benzylphenol) sulfide, 2,2'-bis(4-benzylphenol) sulfide, 2,2'-bis(4,6-dibenzylphenol) sulfide, 2,2'-bis(4-phenylphenol) sulfide, 2,2'-bis(4-phenyl-6-methylphenol) sulfide, 2,2'-bis(4-α,α'-dimethylbenzyl-6-phenyl-phenol) sulfide, 2,2'-bis(4-chlorophenol) sulfide, 2,2'-bis(4,6-dichlorophenol) sulfide, 2,2'-bis(4,5,6-trichlorophenol) sulfide, 2,2'-bis(4-bromophenol) sulfide, 2,2'-bis(4,6-dibromophenol) sulfide, 2,2'-bis(4-hydroxyphenol) sulfide, 2,2'-bis(4,6-dimethoxyphenol) sulfide, 2,2'-bis(4-carboxyphenol) sulfide, 2,2'-bis(4-carbomethoxyphenol) sulfide, 2,2'-bis(4-carbobutoxyphenol) sulfide, 1,1'-bis(2-naphthol) sulfide, 2,2'-bis(1-naphthol) sulfide and the like, 2,2'- bishpenol sulfoxides such as 2,2'-diphenol sulfoxide, 2,2'-bis(4-methylphenol) sulfoxide, 2,2'-bis(6-metylphenol) sulfoxide, 2,2'-bis(4-isopropylphenol) sulfoxide, 2,2'-bis(4-n-butylphenol) sulfoxide, 2,2'-bis(4-sec-butylphenol) sulfoxide, 2,2'-bis(4-tert-butylphenol) sulfoxide, 2,2'-bis(6-tert-butylphenol) sulfoxide, 2,2'-bis(4-tert-amylphenol) sulfoxide, 2,2'-bis(4-tert-octylphenol) sulfoxide, 2,2'-bis(4-nonylphenol) sulfoxide, 2,2'-bis(4-tert-butyl-6-methylphenol) sulfoxide, 2,2'-bis(4-methyl-6-tert-butylphenol) sulfoxide, 2,2'-bis(4,6-dimethylphenol) sulfoxide, 2,2'-bis(4,6-di-tert-butylphenol) sulfoxide, 2,2'-bis(4,5-dimethylphenol) sulfoxide, 2,2'-bis(4-cyclohexylphenol) sulfoxide, 2,2'-bis(4-cyclpohexyl-6-methylphenol) sulfoxide, 2,2'-bis(4,6-dicyclohexylphenol) sulfoxide, 2,2'-bis(4-α,α'-dimethylbenzylphenol) sulfoxide, 2,2'-bis(4-benzylphenol) sulfoxide, 2,2'-bis(4,6-dibenzylphenol) sulfoxide, 2,2'-bis(4-phenylphenol) sulfoxide, 2,2'-bis(4-phenyl-6-methylphenol) sulfoxide, 2,2'-bis(4-α,α'-dimethylbenzyl-6-phenylphenol) sulfoxide, 2,2'-bis(4-chloropheol) sulfoxide, 2,2'-bis(4,6-dichlorophenol) sulfoxide, 2,2'-bis(4,5,6-trichlorophenol) sulfoxide, 2,2'-bis(4-bromophenol) sulfoxide, 2,2'-bis(4,6-dibromophenol) sulfoxide, 2,2'-bis(4-hydroxyphenol) sulfoxide, 2,2'-bis(4,6-dimethoxyphenol) sulfoxide, 2,2'-bis(4-carboxyphenol) sulfoxide, 2,2'-bis(4-carbomethoxyphenol) sulfoxide, 2,2'-bis(4-carbobutoxyphenol) sulfoxide, 1,1'-bis(2-naphthol) sulfoxide, 2,2'-bis(1-naphthol) sulfoxide and the like, 4,4'-bisphenol sulfides such as 4,4'-diphenol sulfide, 4,4'-bis(2-chlorophenol) sulfide, 4,4'-bis(3-chlorophenol) sulfide, 4,4'-bis(2-methylphenol) sulfide, 4,4'-bis(3-methylphenol) sulfide, 4,4'-bis(2,5-dimethylphenol) sulfide, 4,4'-bis(2-isopropyl-5-methylphenol) sulfide, 4,4'-bis(2-methyl-6-tert-butylphenol) sulfide, 4,4'-bis(2,6-tert-butylphenol) sulfide, 4,4'-bis(2-hydroxyphenol) sulfide, 4,4'-bis(2-carboxyphenol) sulfide, 4,4'-bis(2-carbomethoxyphenol) sulfide and the like, and 4,4'-bisphenol sulfoxides such as 4,4'-diphenol sulfoxide, 4,4'-bis(2,5-dimethylphenol) sulfoxide, 4,4'-bis(2-tert-butylphenol) sulfoxide, 4,4'-bis(2-cyclohexylphenol) sulfoxide, 4,4'-bis(2-tert-butyl-5-methylphenol) sulfoxide, 4,4'-bis(2-benzylphenol) sulfoxide, 4,4'-bis(2-methoxyphenol) sulfoxide, 4,4'-bis(2-phenoxyphenol)

sulfoxide, 4,4'-bis(carboxyphenol) sulfoxide, 4,4'-bis(2-carbomethoxyphenol) sulfoxide and the like.

The process of the present invention is usually carried out in an aqueous medium, but an organic solvent instead of water can be used regardless of the solubility of phenolate in water.

The organic solvents used in the process of the present invention include any conventional organic solvents excluding any organic acids which form organic peracids with hydrogen peroxide under the reaction conditions, and more specifically includes aliphatic, alicyclic and aromatic hydrocarbons such as hexane, cyclohexane, heptane, benzene, toluene, xylene and ethyl benzene; aliphatic, alicyclic and aromatic halogenated hydrocarbons such as dichloromethane, chloroform, carbon tetrachloride, dichloroethane, trichloroethane, chlorobenzene and o-dichlorobenzene; alcohols such as methanol, ethanol, propanol and butanol; ethers such as diethyl ether, dibutyl ether, tetrahydrofuran and dioxane; ketones such as acetone and methylethylketone; esters such as acetic acid esters and propionic acid esters; aprotic polar solvents such as N,N-dimethylformamide, dimethylsulfoxide, and N-methyl pyrrolidone, carbon disulfide, and the like.

The above solvents may be used as a mixture thereof, or as a mixture thereof with water.

The use of hydrocarbon and halogenated hydrocarbon solvents immiscible with water specifically such as benzene, toluene, xylene, chlorobenzene, dichloroethane and carbon tetrachloride among the solvents mentioned above, enables the solvents to be recovered by steam distillation after completion of the reaction. The recovered solvents can be directly reused by circulation, or, if required, can be further subjeced to a purification treatment such as distillation for reuse. This results in the reduction of the amount of the solvent used, leading to reduced costs. Also, it results in fewer problems associated with protection of the environment with great industrial advantages.

The solvent is generally used in an amount of from 0.5 to 10 parts by volume and preferably from about 2 to 5 part by volume per one part by weight of the sulfide used as a starting material.

Hydrogen peroxide is used as an aqueous hydrogen peroxide solution at various concentrations, and preferably as aqueous hydrogen peroxide at a concentration in the range of from 30 to 35% due to easiness in its handling. Hydrogen peroxide is usually used in a little excess over the amount theoretically required relative to bisphenols, but may also be used in an amount in the range of from 1.5 to 5.0 times the amount theoretically required. Hydrogen peroxide is added either drop by drop to an alkaline solution of said sulfoxide, or mixed with the solution in advance.

The reaction of the present invention is usually carried out at a temperature of from 30° to 110° C. If the reaction temperature is lower than 30° C., the reaction requires a long period of time, while if the reaction temperature is higher than 110° C., the concentration of hydrogen peroxide is extremely reduced, and unfavorable phenomena such as bubbling take place, which results in preventing the reaction from taking place. The reaction temperature is more preferably from 50° to 100° C. In the practice of the process of the present invention, generally a bisphenol and an equimolar amount of alkali are dissolved in water and/or an organic solvent. While this solution is kept at a temperature of 30°–110° C., aqueous hydrogen peroxide is added thereto drop by drop. After the addition by dropping of the aqueous hydrogen peroxide is completed, the resulting reaction mixture is stirred at that temperature for an additional 30 minutes to 5 hours. After the reaction mixture is allowed to cool to room temperature, a precipitate is formed by neutralizing the reaction mixture directly with acid, by diluting it with water or subjecting it to steam distillation to distill off the solvent after neutralization, or by subjecting the reaction mixture to steam distillation directly as an alkali solution followed by neutralizing it. The precipitate is separated by filtration, washed with water, and dried to obtain bisphenol sulfone derivatives as the final product.

In any of the cases mentioned above, bisphenol sulfone derivatives can be obtained at a high yield of 95% or above as a product of such a high purity as can be directly used without being subjected to additional procedures. Specifically they can be directly used as light stabilizers polyolefin modifiers, lubricant additives, agricultural chemicals, or intermediates thereof.

Bisphenol sulfoxides used in the present invention can be prepared according to known processes, for example, by reacting a substituted phenol with thionyl chloride in the presence of anhydrous aluminum chloride.

In accordance with the present invention, the use of a theoretical amount of hydrogen peroxide causes the reaction to proceed desirably, and even the use of a large excess of hydrogen peroxide causes no problems. Moreover, according to the process of the present invention, no formation of any oxidation by-products is recognized and the corresponding bisphenol sulfone derivatives of extremely high purity can be obtained at an approximately quantitative yield, which results in great industrial advantages.

The process of the present invention is further illustrated by the following examples.

EXAMPLE 1

In a solution of 6 g (0.15 mole) of sodium hydroxide and 100 ml of water was dissolved 24.6 g (0.1 mole) of 2,2'-bis(4-methylphenol) sulfide. While this solution was kept at a temperature of 70°–75° C., 28.3 g (0.25 mole) of 30% aqueous hydrogen peroxide solution was added thereto drop by drop over a period of 30 minutes. The resulting reaction mixture was stirred at that temperature for an additional hour, and then diluted with 100 ml of water. The resulting solution was allowed to cool to room temperature and then was neutralized to form a precipitate. The precipitate was separated by filtration, washed with water, and dried to obtain a yield of 26.8 g (96.4% of theory) of 2,2'-bis(4-methylphenol) sulfone having a melting point of 205°–206° C. The precipitate was further subjected to recrystallization from glacial acetic acid to obtain a pure product melting at a temperature of 207°–208° C. as white needle-like crystals.

The results of elemental analysis were as follows:

|  | C(%) | H(%) | S(%) |
| --- | --- | --- | --- |
| Calculated Values | 60.4 | 5.07 | 11.5 |
| Found Values | 60.7 | 5.12 | 11.7 |

EXAMPLE 2

In a solution of 5 g (0.125 mole) of sodium hydroxide and 100 ml of water was dissolved 26.2 g (0.1 mole) of 2,2'-bis(4-methylphenol) sulfoxide. While this solution was kept at a temperature of 70°–75° C., 17 g (0.15 mole) of 30% hydrogen peroxide solution was added thereto drop by drop over a period of 30 minutes. The resulting reaction mixture was stirred at that temperature for an additional hour, and then diluted with 100 ml of water. The resulting solution was allowed to cool to room temperature and then was neutralized to form a precipitate. The precipitate was separated by filtration, wash with water, and dired to obtain an yield of 27. 1 g (97.5% of theory) of 2,2'-bis(4-metylphenol) sulfone having a melting point of 205°-206° C.

EXAMPLE 3

In 40 ml of ethanol was 28.7 g (0.1 mole) of 2,2'-bis(4-chlorophenol) sulfide. To the resulting solution was added 20 g (0.15 mole) of 30% aqueous sodium hydroxide solution, and then 28.3 g (0.25 mole) of 30% aqueous hydrogen peroxide solution was added thereto drop by drop over a period of 30 minutes, while the solution was kept at a temperature of 65°-70° C. The resulting reaction mixture was stirred at that temperature for an additional hour, and then diluted with 50 ml of water. The resulting solution was allowed to cool to room temperature and then was neutralized to form a precipitate. The precipitate was separated by filtration, washed with water, and dried to obtain a yield of 30.9 g (97% of theory) of 2,2'-bis(4-chlorophenol) sulfone having a melting point of 189°-190° C. The precipitate was further subjected to recrystallization from glacial acetic acid to obtain a pure product melting at a temperature of 191°-192° C. as white needle-like crystals.

The results of elemental analysis were as follows:

|  | C(%) | H(%) | Cl(%) | S(%) |
|---|---|---|---|---|
| Calculated Values | 45.2 | 2.52 | 22.2 | 10.0 |
| Found Values | 45.6 | 2.48 | 22.5 | 10.5 |

EXAMPLES 4-9

The procedure of Example 3 was repeated except that 2,2'-bisphenol sulfides were used to obtain the corresponding 2,2'-bisphenol sulfones with the results as shown in Table I.

TABLE 1

| Example | 2,2'-bisphenol sulfone | Yield (%) | m.p. (°C.) | Values by Elemental Analysis (%) | | | |
|---|---|---|---|---|---|---|---|
| | | | | C | H | S | Br |
| 4 | 2,2'-diphenol sulfone | 98 | 190-191 | 57.3 (57.6) | 4.11 (4.03) | 12.4 (12.8) | |
| 5 | 2,2'-bis(4-bromophenol) sulfone | 95.5 | 209-210 | 35.7 (35.3) | 1.95 (1.97) | 7.79 (7.85) | 39.5 (39.2) |
| 6 | 2,2'-bis(4-cyclohexylphenol) sulfone | 97.0 | 177-179 | 69.9 (69.5) | 7.33 (7.29) | 7.81 (7.73) | |
| 7 | 2,2'-bis(4-α,α'-dimethylbenzylphenol) sulfone | 98.0 | 139-140 | 74.2 (74.1) | 6.38 (6.21) | 6.34 (6.59) | |
| 8 | 2,2'-bis(4-phenylphenol) sulfone | 95.0 | 221-222 | 71.9 (71.6) | 4.63 (4.51) | 7.91 (7.97) | |
| 9 | 1,1'-bis(2-naphthol) sulfone | 95.0 | 235 (decomposition) | 68.0 (68.6) | 4.03 (4.03) | 9.19 (9.15) | |

*Values in brackets show calculated values.

EXAMPLE 10

In 50 ml of 1,2-dichloroethane was dissolved 33 g (0.1 mole) of 2,2'-bis(4-tert-butylphenol) sulfide. To this solution was added 20 g (0.15 mole) of 30% sodium hydroxide aqueous solution, and then 28.3 g (0.25 mole) of 30% aqueous hydrogen peroxide was added thereto drop by drop over a period of 30 minutes, while the solution was kept at a temperature of 45°-50° C. The resulting reaction mixture was stirred at that temperature for additional three hours, and then was neutralized. Then, the reaction mixture was subjected to steam distillation to distill off 1,2-dichloroethane, forming a precipitate. After being allowed to cool to room temperature, the precipitate was separated by filtration, washed with water, and dried to obtain 35.5 g (98% of theory) of 2,2'-bis(4-tert-butylphenol) sulfone having a melting point of 129°-130° C. The precipitate was subjected to recrystallization from n-hexane to obtain a pure product melting at a temperature of 131°-132.5° C. as white needle-like crystals.

The results of elemental analysis were as follows:

|  | C(%) | H(%) | S(%) |
|---|---|---|---|
| Calculated Values | 66.3 | 7.23 | 8.85 |
| Found Values | 66.1 | 7.50 | 8.66 |

EXAMPLE 11

The procedure of Example 10 was repeated except that 2,2'-bis(4,6-dichlorophenol) sulfide was used to obtain 2,2'-bis(4,6-dichlorophenol) sulfone having a melting point of 168°-170° C. at an yield of 96%.

The thus-obtained product was subjected to recrystallization from ethanol to obtain a pure product melting at a temperature of 170°-171° C. as white needle-like crystals.

The results of elemental analysis were as follows:

|  | C(%) | H(%) | Cl(%) | S(%) |
|---|---|---|---|---|
| Calculated Values | 37.1 | 1.56 | 36.5 | 8.26 |
| Found Values | 37.4 | 1.61 | 36.6 | 8.42 |

EXAMPLE 12

A mixture of 44.2 g (0.1 mole) of 2,2'-bis(4-tert-octylphenol) sulfide, 30 g (0.15 mole) of 20% aqueous sodium hydroxide solution, 28.3 g (0.25 mole) of 30% aqueous hydrogen peroxide solution and 60 ml of benzene was stirred at a temperature of 70°-75° C. for 3 hours, and then was subjected to steam distillation to distill off benzene. The resulting reaction mixture was neutralized to form a precipitate. After being allowed to cool to room temperature, the precipitate was separated by filtration, washed with water, and dried to obtain 46.6 g (98.5% of theory) of 2,2'-bis(4-tert-octylphenol) sulfone having a melting point of 142°–143° C.

The above product was further subjected to recrystallization from glacial acetic acid to obtain a pure product melting at a temperature of 143°–145° C. as white needle-like crystals.

The results of elemental analysis were as follows:

|  | C(%) | H(%) | S(%) |
|---|---|---|---|
| Calculated Values | 70.9 | 8.92 | 6.75 |
| Found Values | 70.7 | 8.78 | 6.77 |

EXAMPLE 13

The procedure of Example 12 was repeated except that 2,2'-bis(4-methyl-6-tert-butylphenol) sulfide was used to obtain 2,2'-bis(4-methyl-6-tert-butylphenol) sulfone having a melting point of 130°–131° C. at an yield of 95.5%.

The above product was subjected to recrystallization from ethanol to obtain a pure product melting at a temperature of 132°–134° C. as white needle-like crystals.

The results of elemental analysis were follows:

|  | C(%) | H(%) | S(%) |
|---|---|---|---|
| Calculated Values | 67.6 | 7.74 | 8.21 |
| Found Values | 67.7 | 7.82 | 8.01 |

EXAMPLE 14

In 30 ml of chlorobenzene was dissolved 35.8 g (0.1 mole) of 2,2'-bis(4-tert-amylphenol) sulfide. To this solution was added 36.5 g (0.13 mole) of 20% aqueous potassium hydroxide solution. To the resulting solution was added drop by drop 28.3 g (0.25 mole) of 30% aqueous hydrogen peroxide solution over a period of 30 minutes, while the solution was kept at a temperature of 75°–80° C. The resulting reaction mixture was stirred at that temperature for an additional hour followed by neutralization. The reaction mixture was subjected to steam distillation to distill off chlorobenzene, forming a precipitate. After being allowed to cool to room temperature, the precipitate was separated by filtration, washed with water, and dried to obtain an yield of 37.6 g (96.5% of theory) of 2,2'-bis(4-tert-amylphenol) sulfone having a melting point of 117°–118° C.

The above product was subjected to recrystallization from n-hexane to obtain a pure product melting at a temperature of 119°–120° C. as white prism-like crystals.

The results of elemental analysis are as follows:

|  | C(%) | H(%) | S(%) |
|---|---|---|---|
| Calculated Values | 67.6 | 7.74 | 8.21 |
| Found Values | 67.4 | 7.82 | 8.08 |

EXAMPLE 15

In 40 ml of ethanol was dissolved 29.3 g (0.1 mole) of 2,2'-bis(4-chlorophenol) sulfoxide. To this solution was added 20 g (0.15 mole) of 30% aqueous sodium hydroxide solution, and then 17 g (0.15 mole) of 30% aqueous hydrogen peroxide solution was added thereto drop by drop over a period of 30 minutes, while the soltuion was kept at a temperature of 65°–70° C. The resulting reaction mixture was stirred at that temperature for an additional hour, and then diluted with 50 ml of water. After being allowed to cool to room temperature, the reaction mixture was neutralized to form a precipitate. The precipitate was separated by filtration, washed with water, and dried to obtain 31.2 g (98% theory) of 2,2'-bis(4-chlorophenol) sulfone having a melting point of 190°–191° C.

EXAMPLE 16

The procedure of Example 15 was repeated except that 2,2'-bis(4-bromophenol) sulfoxide was used to obtain 2,2'-bis(4-bromophenol) sulfone melting at a temperature of 207°–208° C. at an yield of 97%.

EXAMPLE 17

In 50 ml of 1,2-dichloroethane was dissolved 34.6 g (0.1 mole) of 2,2'-bis(4-tert-butylphenol) sulfoxide. To this solution was added 20 g (0.15 mole) of aqueous sodium hydroxide solution, and then 17 g (0.15 mole) of 30% aqueous hydrogen peroxide solution was added thereto drop by drop over a period of 30 minutes, while the solution was kept at a temperature of 45°–50° C. The resulting reaction mixture was stirred at that temperature for additional three hours followed by neutralization. The reaction mixture was further subjected to steam distillation to form a precipitate. After being allowed to cool to room temperature, the precipitate was separated by filtration, washed with water, and dried to obtain 35.6 g (98.5% theory) of 2,2'-bis(4-tert-butylphenol) sulfone having a melting point of 130°–132° C.

EXAMPLE 18

The procedure of Example 17 was repeated except that 2,2'-bis(4,6-dichlorophenol) sulfoxide was used to obtain 2,2'-bis(4,6-dichlorophenol) sulfone having a melting point of 169°–170° C. at an yield of 97.5%.

EXAMPLE 19

A mixture of 45.8 g (0.1 mole) of 2,2'-bis(4-tert-octylphenol) sulfoxide, 30 g (0.15 mole) of 20% aqueous sodium hydroxide solution, 17 g (0.15 mole) of 30% aqueous hydrogen peroxide solution, and 60 ml of benzene was stirred at a temperature of 70°–75° C. for 3 hours, and then the resulting reaction mixture was subjected to steam distillation to distill off benzene. The reaction mixture was neutralized to form a precipitate. After being allowed to cool to room temperature, the precipitate was separated by filtration, washed with water, and dried to obtain an yield of 46.9 g (99% of theory) of 2,2'-bis(4-tert-octylphenol) sulfone having a melting point of 142°–143° C.

EXAMPLE 20

The procedure of Example 19 was repeated except that 2,2'-bis(4-methyl-6-tert-butylphenol) sulfoxide was used to obtain 2,2'-bis(4-methyl-6-tert-butylphenol) sulfone having a melting point of 130°–131° C.

EXAMPLE 21

In 30 ml of chlorobenzene was dissolved 37.4 g (0.1 mole) of 2,2'-bis(4-tert-amylphenol) sulfoxide. To this solution was added 36.5 g (0.13 mole) of 20% aqueous potassium hydroxide solution, and then 17 g (0.15 mole) of 30% aqueous hydrogen peroxide solution was added thereto drop by drop over a period of 30 minutes, while the solution was kept at a temperature of 75°-80° C. The resulting reaction mixture was stirred at that temperature for an additional hour followed by neutralization. The reaction mixture was further subjected to steam distillation to distill off chlorobenzene, forming a precipitate. After being allowed to cool to room temperature, the precipitate was separated by filtration, washed with water, and dried to obtain 38 g (97.5% of theory ) of 2,2'-bis(4-tert-amylphenol) sulfone having a melting point of 117°-118° C.

EXAMPLE 22

In a solution of 5 g (0.125 mole) of sodium hydroxide and 100 ml of water was dissolved 21.8 g (0.1 mole) of 4,4'-bisphenol sulfide. To this solution was added drop by drop 28.3 g (0.25 mole) of 30% aqueous hydrogen solution peroxide over a period of 30 minutes, while the solution was kept at a temperature of from 60°-65° C. The resulting reaction mixture was stirred at that temperature for additional two hours. After being allowed to cool to room temperature, the reaction mixture was neutralized to form a percipitate. The precipitate was separated by filtration, washed with a cold water, and dried to obtain 23.5 g (94% theory) of 4,4'-diphenol sulfone having a melting point of 245°-246° C.

The above product was subjected to recrystallization from water to obtain a pure product having a melting point of 247°-248° C. as white needle-like crystals.

EXAMPLES 23-25

The procedure of Example 22 was repeated except that 4,4'-bisphenol sulfides were used to obtain the corresponding sulfones with the results as shown below.

| Example | Final Product | Yield (%) | m.p. (°C.) |
|---|---|---|---|
| 23 | 4,4'-bis(2-methylphenol) sulfone | 95.5 | 270-271 |
| 24 | 4,4'-bis(3-methylphenol) sulfone | 95 | 205-206 |
| 25 | 4,4'-bis(3-chlorophenol) sulfone | 97 | 219-220 |

EXAMPLE 26

In 80 ml of ethanol was dissolved 27.7 g (0.1 mole) of 4,4'-bis(2-chlorophenol) sulfide. To this solution was added a solution obtained by dissolving 5 g (0.125 mole) of sodium hydroxide in 20 ml of water. To the resulting solution was added drop by drop 28.3 g (0.25 mole) of 30% aqueous hydrogen peroxide solution over a period of 30 minutes, while the solution was kept at a temperature of 70°-75° C. The resulting reaction mixture was stirred at that temperature for additional two hours. After being allowed to cool to room temperature, the reaction mixture was neutralized to form a precipitate. The precipitate was separated by filtration, washed with water, and dried to obtain 29.0 g (94% of theory) of 4,4'-bis(2-chlorophenol) sulfone having a melting point of 195°-197° C.

The above product was further subjected to recrystallization from a mixture of ethanol and water to obtain a pure product having a melting point of 196°-197° C. as white needle-like crystals.

EXAMPLES 27-28

The procedure of Example 26 was repeated except that 4,4'-bisphenol sulfides were used as starting materials to obtain the corresponding sulfones with the results as shown below.

| Example | Final Product | Yield (%) | m.p.(°C.) |
|---|---|---|---|
| 27 | 4,4'-bis(2,5-dimethylphenol) sulfone | 96 | 256-257 |
| 28 | 4,4'-bis(2-isopropyl-5-methylphenol) sulfone | 95 | 218-220 |

EXAMPLE 29

In a solution of 7.0 g (0.125 mole) of potassium hydroxide and 100 ml of water was dissolved 23.4 g (0.1 mole) of 4,4'-diphenol sulfoxide. To this solution was added drop by drop 14.2 g (0.125 mole) of 30% aqueous hydrogen peroxide solution over a period of 30 minutes, while the solution was kept at a temperature of 55°-60° C. The resulting reaction mixture was stirred at that temperature for additional three hours. After being allowed to cool to room temperature, the reaction mixture was neutralized to form a precipitate. The precipitate was separated by filtration, washed with cold water, and dried to obtain 23.9 g (96% of theory) of 4,4'-diphenol sulfone.

EXAMPLE 30

In 150 ml of xylene was dissolved 37.4 g (0.1 mole) of 4,4'-bis(2-tert-butyl-5-methylphenol) sulfoxide. To this solution was added 36.5 g (0.13 mole) of 20% aqueous potassium hydroxide solution, and then 14.2 g (0.125 mole) of 30% aqueous hydrogen peroxide solution was added thereto drop by drop over a period of 30 minutes, while the solution was kept at a temperature of 75°-80° C. The resulting reaction mixture was stirred at that temperature for additional two hours followed by neutralization. The reaction mixture was further subjected to steam distillation to distill off xylene, forming a precipitate. After being allowed to cool to room temperature, the precipitate was separated by filtration, washed with water, and dried to obtain 38.0 g (98% of theory) of 4,4'-bis(2-tert-butyl-5-methylphenol) sulfone having a melting point of 248°-250° C. The above product was further subjected to recrystallization from ethanol to obtain a pure product having a melting point of 250°-251° C. as white needle-like crystals.

EXAMPLES 31-32

The procedure of Example 30 was repeated except that 4,4'-diphenol sulfoxide were used as starting materials to obtain the corresponding sulfones with the results as shown below.

| Example | Final Product | Yield (%) | m.p.(°C.) |
|---|---|---|---|
| 31 | 4,4'-bis(2-phenylphenol) sulfone | 97 | 247-248 |
| 32 | 4,4'-bis(2-carbomethoxyphenol) sulfone | 95 | 204-205 |

EXAMPLE 33

In a solution of 13.2 g (0.33 mole) of sodium hydroxide and 150 ml of water was dissolved 32.2 g (0.1 mole) of 4,4'-bis(2-carboxyphenol) sulfoxide. To this solution was added drop by drop 14.2 g (0.125 mole) of 30% aqueous hydrogen peroxide solution over a period of 30 minutes, while the solution was kept at a temperature of 50°-60° C. The resulting reaction mixture was stirred at that temperature for additional four hours. After being allowed to cool to room temperature, the reaction mixture was neutralized to form a precipitate. The precipitate was separated by filtration, washed with water, and dried to obtain 33 g (97.5% of theory) of 4,4'-bis(2-carboxyphenol) sulfone having a melting point of 301°–303° C.

The above product was further subjected to recrystallization from a mixture of acetic acid and water to obtain a pure product having a melting point of 303°–304° C. as white needle-like crystals.

What is claimed is:

1. A process for preparing a bisphenol sulfone compound represented by the general formula (I)

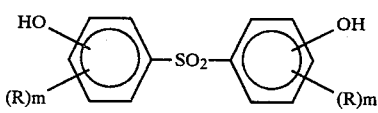 (I)

where R stands for hydrogen, a halogen, an alkyl group, a cycloalkyl group, an aryl group, an aralkyl group, hydroxyl group, an alkoxy group, allyloxy group, carboxyl group, or a carboalkoxy group, m is an integer of from 1 to 3, and when m is 2 or more each group represented by R may be identical or different and adjacent Rs may be combined to form a benzene ring, which comprises oxidizing a compound represented by the general formula (II)

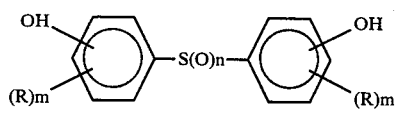 (II)

where R and m have the same meanings as defined for the compounds of formula (I), and n is zero or 1, with hydrogen peroxide in the presence of an alkali metal hydroxide, the amount of said alkali metal hydroxide being equimolar relative to said compound of formula (II) in water or in water plus an organic solvent which does not form any organic peracids under reaction conditions to form said bisphenol sulfone compound, said organic solvent being selected from the group consisting of aliphatic, alicyclic and aromatic hydrocarbons, halogenated aliphatic, alicyclic and aromatic hydrocarbons, alcohols, ethers, esters, ketones, aprotic polar solvents, carbon disulfide, and mixtures thereof.

2. A process according to claim 1, wherein the compounds of the general formula (II) are 2,2'-bisphenol sulfides and 2,2'-bisphenol sulfoxides represented by the general formula (III)

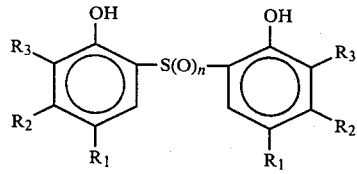 (III)

where $R_1$, $R_2$ and $R_3$ stand for hydrogen, a halogen, an alkyl group, a cycloalkyl group, an aryl group, an aralkyl group, hydroxyl group, an alkoxy group, allyloxy group, carboxyl group or a carboalkoxy group, being identical to or different from each other, or $R_1$ and $R_2$ or $R_2$ and $R_3$ may form a benzene ring with the carbons of the benzene nucleus to which they are bonded, and n is zero or 1.

3. A process according to claim 1, wherein the compounds of the general formula (II) are 4,4'-bisphenol sulfides and 4,4'-bisphenol sulfoxides represented by the general formula (IV)

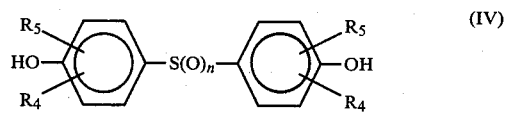 (IV)

where $R_4$ and $R_5$ stand for hydrogen, a halogen, an alkyl group, a cycloalkyl group, an aryl group, an aralkyl group, hydroxyl group, an alkoxy group, allyloxy group, carboxyl group, or a carboalkoxy group, wherein $R_4$ and $R_5$ can be the same or different, or $R_4$ and $R_5$ may form a benzene ring with the carbons of the benzene ring to which they are bonded, and n is zero or 1.

4. A process according to claim 1, wherein said oxidizing is in water plus an organic solvent selected from the group consisting of aliphatic, alicyclic and aromatic hydrocarbons, alcohols, ethers, esters, ketones, aprotic polar solvents, carbon disulfide and mixtures thereof.

5. A process according to claim 1, wherein a hydrocarbon or halogenated hydrocarbon immiscible with water is used as said solvent, the reaction mixture is neutralized after the completion of reaction, the solvent is recovered by steam distillation, and the final product is obtained as a precipitate.

6. A process according to claim 5, wherein the hydrocarbon or halogenated hydrocarbon immiscible with water is benzene, toluene, xylene, chlorobenzene, dichloroethane or carbon tetrachloride.

7. A process according to claim 1, wherein the amount of said hydrogen peroxide is from the theoretical amount thereof required for oxidizing the compound of formula II to the sulfone compound to 5.0 times said theoretical amount.

8. A process according to claim 1, wherein the amount of alkali is from 1 to 5 moles per mole of the compound of general formula II.

9. A process according to claim 1, wherein said alkali metal hydroxide is selected from the group consisting of sodium hydroxide, potassium hydroxide, and lithium hydroxide.

10. A process according to claim 1, wherein the reaction temperature is in the range of from 30° to 110° C.

11. A process according to claim 1, wherein the reaction is effected in an aqueous medium.

12. A process as claimed in claims 1, 2, or 3 wherein said alkyl group has 1–9 carbons, said aryl group is a phenyl group, said aralkyl group has 7–9 carbon atoms, and said carboalkoxy group has 2–5 carbon atoms.

13. A process as claimed in claim 12 wherein said cycloalkyl group is a cyclohexyl group and said alkoxy group is a methoxy group.

* * * * *